(12) United States Patent
Sugita et al.

(10) Patent No.: US 8,348,943 B2
(45) Date of Patent: Jan. 8, 2013

(54) HIGH FREQUENCY TREATMENT TOOL FOR ENDOSCOPE

(75) Inventors: Noriyuki Sugita, Saitama (JP); Satoshi Kidooka, Chiba (JP); Takashi Toyonaga, Osaka (JP)

(73) Assignee: Hoya Corporation, Tokyo (JP)

( * ) Notice: Subject to any disclaimer, the term of this patent is extended or adjusted under 35 U.S.C. 154(b) by 1362 days.

(21) Appl. No.: 11/326,411

(22) Filed: Jan. 6, 2006

(65) Prior Publication Data

US 2006/0155271 A1   Jul. 13, 2006

(30) Foreign Application Priority Data

Jan. 7, 2005  (JP) ................................ 2005-001984
Jan. 7, 2005  (JP) ................................ 2005-001985

(51) Int. Cl.
*A61B 18/14* (2006.01)
(52) U.S. Cl. .......................................... 606/46; 606/45
(58) Field of Classification Search .................. 606/41, 606/45–50
See application file for complete search history.

(56) References Cited

U.S. PATENT DOCUMENTS

| | | | | |
|---|---|---|---|---|
| 3,532,095 A * | 10/1970 | Miller et al. | ..................... | 606/45 |
| 5,300,069 A * | 4/1994 | Hunsberger et al. | ............. | 606/37 |
| 5,569,164 A * | 10/1996 | Lurz | ............................. | 600/158 |
| 5,766,169 A | 6/1998 | Fritzsch et al. | | |
| 6,093,195 A | 7/2000 | Ouchi | | |
| 6,190,384 B1 * | 2/2001 | Ouchi | ............................. | 606/47 |
| 6,423,060 B1 | 7/2002 | Ouchi | | |
| 6,558,385 B1 * | 5/2003 | McClurken et al. | ............ | 606/50 |
| 6,953,430 B2 | 10/2005 | Kidooka | | |
| 8,016,825 B2 | 9/2011 | Okada | | |
| 2003/0078644 A1 * | 4/2003 | Phan | ............................. | 607/119 |
| 2004/0172018 A1 * | 9/2004 | Okada | ............................. | 606/46 |
| 2004/0186348 A1 | 9/2004 | Kidooka | | |
| 2004/0210215 A1 | 10/2004 | Okada | | |
| 2004/0210284 A1 | 10/2004 | Okada | | |
| 2005/0080411 A1 | 4/2005 | Ouchi | | |

(Continued)

FOREIGN PATENT DOCUMENTS

DE   4420608   12/1995

(Continued)

OTHER PUBLICATIONS

English Language Abstract of JP 6-292685.

(Continued)

*Primary Examiner* — Michael Peffley
*Assistant Examiner* — Samantha Good
(74) *Attorney, Agent, or Firm* — Greenblum & Bernstein P.L.C.

(57) ABSTRACT

A high frequency treatment tool for an endoscope includes a flexible insulating tube to be inserted into and pulled out of an accessory channel of the endoscope, the flexible insulating tube including a wire insertion channel and a water channel through which water is conveyed, a conductive wire configured to move back and forth in an axis line direction thereof through the wire insertion channel, and an electrode configured to project and recede from a distal end of the flexible insulating tube. The wire insertion channel and the water channel are separately formed in an axis line direction of the flexible insulating tube such that each of axis lines of the wire insertion channel and the water channel is eccentric with respect to the axis line of the flexible insulating tube. The electrode is coupled to the conductive wire such that an axis line of the electrode is eccentric with respect to an axis line of the conductive wire.

10 Claims, 13 Drawing Sheets

U.S. PATENT DOCUMENTS

2005/0215996 A1  9/2005  Ouchi

FOREIGN PATENT DOCUMENTS

| DE | 102004017469 | 11/2004 |
|---|---|---|
| JP | 6-292685 | 10/1994 |
| JP | 10-165359 | 6/1998 |
| JP | 2004-275548 | 10/2004 |
| JP | 2004-313537 | 11/2004 |

OTHER PUBLICATIONS

Japanese Office Action (Notification of Reasons for Refusal) mailed Nov. 4, 2010 that issued with respect to counterpart Japanese Patent Application No. 2005-001985, along with an English language translation thereof.

Germany Office action, dated Feb. 24, 2012 along with an english translation thereof.

\* cited by examiner

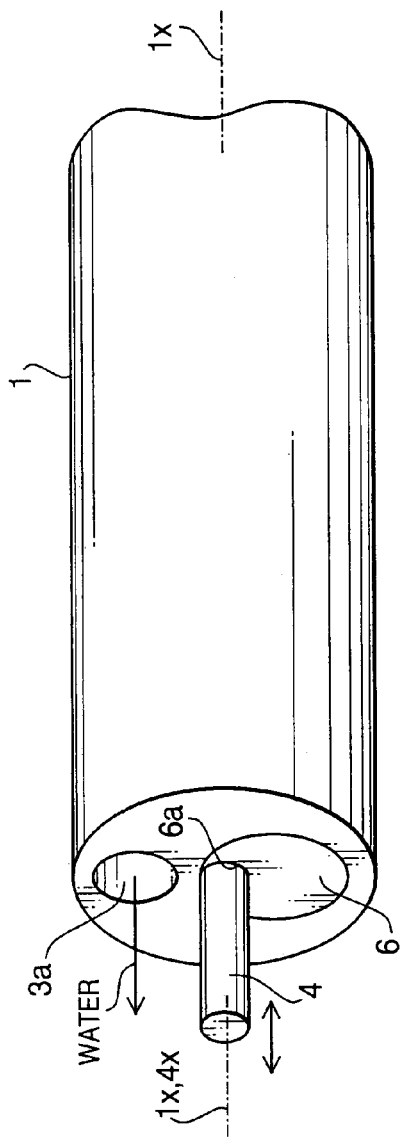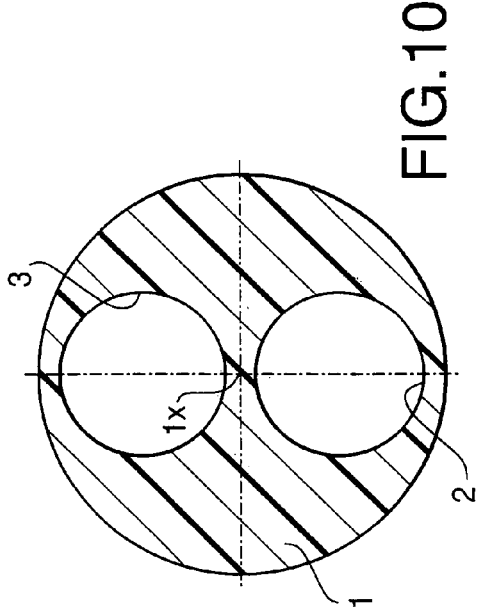

HIGH FREQUENCY TREATMENT TOOL FOR ENDOSCOPE

BACKGROUND OF THE INVENTION

The present invention relates to a high frequency treatment tool, which is provided with a needle-shaped high frequency electrode configured to project forward and recede from a distal end of a sheath to be inserted into and pulled out of an accessory channel of an endoscope.

A high frequency treatment tool for an endoscope, which is used to give treatments of incision/coagulation for body tissues such as mucous tissues, is preferred to be configured to rinse out the surface of the mucous tissues as an object of such treatments before incision of the surface and rinse off cauterized pieces of the mucous tissues, which are burnt to adhere to an electrode and/or its neighboring portions, during the incision.

For this reason, a high frequency treatment tool for an endoscope has been developed, which includes a high frequency electrode provided in an electric insulating sheath to be inserted into and pulled out of an accessory channel of the endoscope, the high frequency electrode being configured to project forward and recede from a distal end of the sheath according to an operation at an operator's hand side of the sheath. In addition, the high frequency treatment tool is configured such that space surrounding the high frequency electrode (and an operating wire coupled with the high frequency electrode) is employed as a water channel through which water to be squirted out of the distal end of the sheath is conveyed. Such a high frequency treatment tool, for example, is disclosed in Japanese Unexamined Patent Publication No. HEI6-292685.

However, when the space surrounding the high frequency electrode is employed as a water channel, the delivered water amounts and/or water flow conditions are quite different between both states of the high frequency electrode projecting and receding from the sheath. Therefore, such a high frequency treatment tool is hard to use.

A high frequency treatment tool, in which there are separately provided a wire insertion channel through which an operating wire is inserted and a water channel in parallel with one another, is considered as a solution to overcome the above problem. However, in such a high frequency treatment tool, when a high frequency electrode is arranged on an axis line of a sheath, a cross-sectional area of the water channel is restricted to be small. On the other hand, when the high frequency electrode is not located on the axis line of the sheath, it is likely to be hard to use because it is difficult to grasp the location of the needle-shaped high frequency electrode during the incision operation.

Further, in such a high frequency treatment tool, since water squirted out of a distal end of the water channel does not reach a tip of the high frequency electrode, it is impossible to efficiently rinse off the cauterized pieces of the mucous tissues, which are generated around the high frequency electrode during the incision operation. Thereby, the incision operation may be cumbersome.

SUMMARY OF THE INVENTION

The present invention is advantageous in that a easy-to-use high frequency treatment tool for an endoscope is provided that includes a high frequency electrode configured to project and recede on an axis line of a sheath without the delivered water amount and/or a water flow condition being affected by projecting/receding states of the high frequency electrode.

According to an aspect of the present invention, there is provided a high frequency treatment tool for an endoscope, which is provided with a flexible insulating tube to be inserted into and pulled out of an accessory channel of the endoscope, the flexible insulating tube including a wire insertion channel and a water channel through which water is conveyed, a conductive wire configured to move back and forth in an axis line direction thereof through the wire insertion channel, and an electrode configured to project and recede from a distal end of the flexible insulating tube. The wire insertion channel and the water channel are separately formed in an axis line direction of the flexible insulating tube such that each of axis lines of the wire insertion channel and the water channel is eccentric with respect to the axis line of the flexible insulating tube. The electrode is coupled to the conductive wire such that an axis line of the electrode is eccentric with respect to an axis line of the conductive wire.

Optionally, the electrode may be configured to project and recede from the distal end of the flexible insulating tube on the axis line of the flexible insulating tube.

Optionally, the electrode may be coupled to the conductive wire with each other's side faces being directly fixed.

Still optionally, the electrode may be coupled to the conductive wire with each other's side faces being directly fixed by silver-alloy brazing.

Optionally, the high frequency treatment tool may further include a regulating member provided at the distal end portion of the flexible insulating tube, the regulating member being configured to regulate movement of the electrode such that the electrode stably projects and recedes from the distal end of the flexible insulating tube.

Further optionally, the regulating member may include a penetrating hole configured to guide the electrode and prevent the conductive wire from getting therein.

Yet optionally, the flexible insulating tube may further include an opening provided at the distal end portion thereof, the opening integrating the wire insertion channel and the water channel. Optionally, the regulating member may be attached in the opening.

Optionally, the flexible insulating tube may be made of an ethylene tetrafluoride resin.

Optionally, at least one of the conductive wire and the electrode may be made of a stainless steel.

Optionally, the high frequency treatment tool may further include a nozzle formed at the distal end portion thereof, the nozzle being configured to direct water conveyed through the water channel to the electrode.

According to another aspect of the present invention, there is provided a high frequency treatment tool for an endoscope, which is provided with a flexible insulating tube to be inserted into and pulled out of an accessory channel of the endoscope, the flexible insulating tube including a wire insertion channel and a water channel through which water is conveyed, the wire insertion channel and the water channel being separately formed in an axis line direction of the flexible insulating tube, a conductive wire configured to move back and forth in an axis line direction thereof through the wire insertion channel, an electrode configured to project and recede from a distal end of the flexible insulating tube, and a nozzle formed at the distal end portion of the flexible insulating tube, the nozzle being configured to direct water conveyed through the water channel to the electrode.

Optionally, the high frequency treatment tool may further include a regulating member provided at the distal end portion of the flexible insulating tube, the regulating member being configured to regulate movement of the electrode such that the electrode stably projects and recedes from the distal end of the flexible insulating tube. Optionally, at least a part of the nozzle may be formed by the regulating member.

According to a further aspect of the present invention, there is provided a high frequency treatment tool for an endoscope, which is provided with a flexible insulating tube to be inserted into and pulled out of an accessory channel of the endoscope, the flexible insulating tube including a wire insertion channel and a water channel through which water is conveyed, the wire insertion channel and the water channel being separately formed in an axis line direction of the flexible insulating tube such that each of axis lines of the wire insertion channel and the water channel is eccentric with respect to the axis line of the flexible insulating tube, a conductive wire configured to move back and forth in an axis line direction thereof through the wire insertion channel, an electrode coupled to the conductive wire such that an axis line of the electrode is eccentric with respect to an axis line of the conductive wire, the electrode being configured to project and recede from a distal end of the flexible insulating tube on the axis line of the flexible insulating tube, and a regulating member provided at the distal end portion of the flexible insulating tube, the regulating member being configured to regulate movement of the electrode such that the electrode stably projects and recedes from the distal end of the flexible insulating tube.

BRIEF DESCRIPTION OF THE ACCOMPANYING DRAWINGS

FIG. 9 is a perspective external view of the distal end portion of the high frequency treatment tool in the first embodiment according to the present invention;

FIG. 10 is a cross-sectional view of a multi-lumen tube, along a plane perpendicular to an axis line thereof, which constitutes a sheath of a high frequency treatment tool in a second embodiment according to the present invention;

DETAILED DESCRIPTION OF THE EMBODIMENTS

First Embodiment

Figure 2:
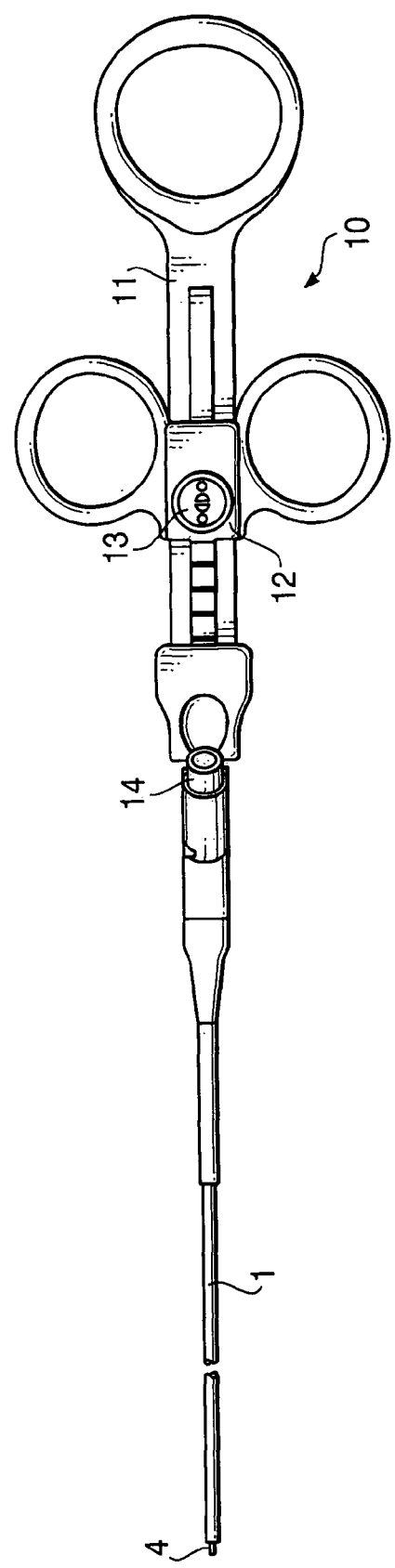
FIG. 2 is a top view showing the overall configuration of the high frequency treatment tool in the first embodiment according to the present invention.
Figure 3:
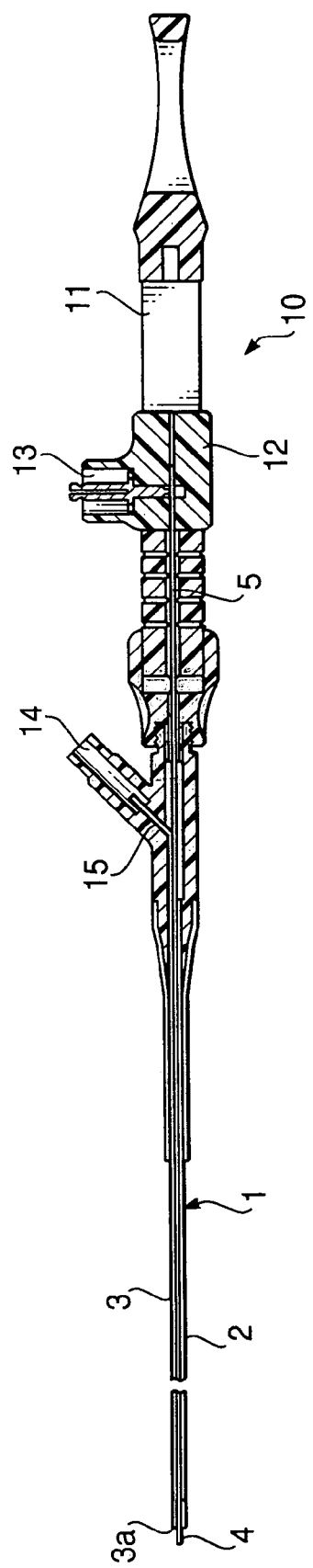
FIG. 3 is a cross-sectional side view showing the overall configuration of the high frequency treatment tool in the first embodiment according to the present invention.

Referring to the accompanying drawings, embodiments of the present invention will be described. FIGS. 2 and 3 are a top view and a cross-sectional side view showing the overall configuration of a high frequency treatment tool for an endoscope in a first embodiment according to the present invention, respectively. A sheath 1, which is configured with a flexible tube made of an electric insulating synthetic resin such as an ethylene tetrafluoride resin, is formed, with a diameter of 2 mm and a length of 1 to 2 m, so as to be able to be inserted into and pulled out of an accessory channel (not shown) of the endoscope.

Figure 4:
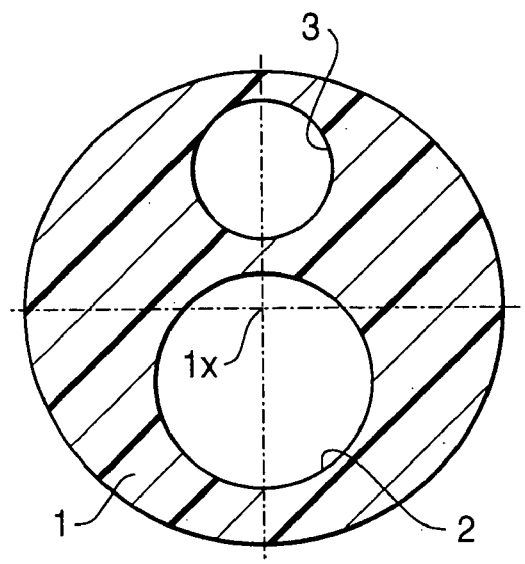
FIG. 4 is a cross-sectional view of a multi-lumen tube, along a plane perpendicular to an axis line thereof, which constitutes a sheath of the high frequency treatment tool in the first embodiment according to the present invention.

The sheath 1, as a cross-sectional view thereof is shown in FIG. 4, is a so-called multi-lumen tube that is provided with a couple of penetrating channels, i.e., a wire insertion channel 2 and a water channel 3 formed side by side along an axis line direction of the sheath 1. Each of axis lines of the wire insertion channel 2 and the water channel 3 is eccentric with respect to an axis line 1x of the sheath 1. It is noted that the axis line of the sheath 1 is included in the wire insertion channel 2.

Referring to FIGS. 2 and 3, at a distal end of the sheath 1, there is provided a needle-shaped high frequency electrode 4, which is configured to be able to project and recede from the distal end of the sheath 1. An operating portion 10 for controlling the high frequency electrode 4 to project or recede is coupled with a rear anchor side (that is, an operator's hand side) of the sheath 1.

Through the wire insertion channel 2 of the sheath 1, there is inserted a conductive operating wire 5, which is, for example, made of a stainless twisted wire, over the entire length of the wire insertion channel 2. The operating wire 5 is configured to be able to move back and forth in the axis line direction thereof through the wire insertion channel 2. The high frequency electrode 4 is connected to a distal end of the operating wire 5.

A rear anchor of the operating wire 5 is connected to a slidable operating member 12 that is provided slidably with respect to a main body 11 of the operating portion 10. Operating the slidable operating member 12 makes it possible for the high frequency electrode 4 to project and recede from the distal end of the sheath 1 via the operating wire 5. In addition, it is possible to supply a high frequency current to the high frequency electrode 4 via the operating wire 5 by connecting a high frequency power cord (not shown) to a joining terminal 13 provided at the slidable operating member 12.

A rear anchor of the water channel 3 in the sheath 1 is connected in communication with a filling pipe sleeve 14 provided at the operating portion 10 via a connecting tube 15. Accordingly, by connecting an injection tool (not shown) to the filling pipe sleeve 14, it is allowed to squirt water forward out of a squirt hole 3a at the distal end, located at the leading edge face of the sheath 1, of the water channel 3.

Figure 1:
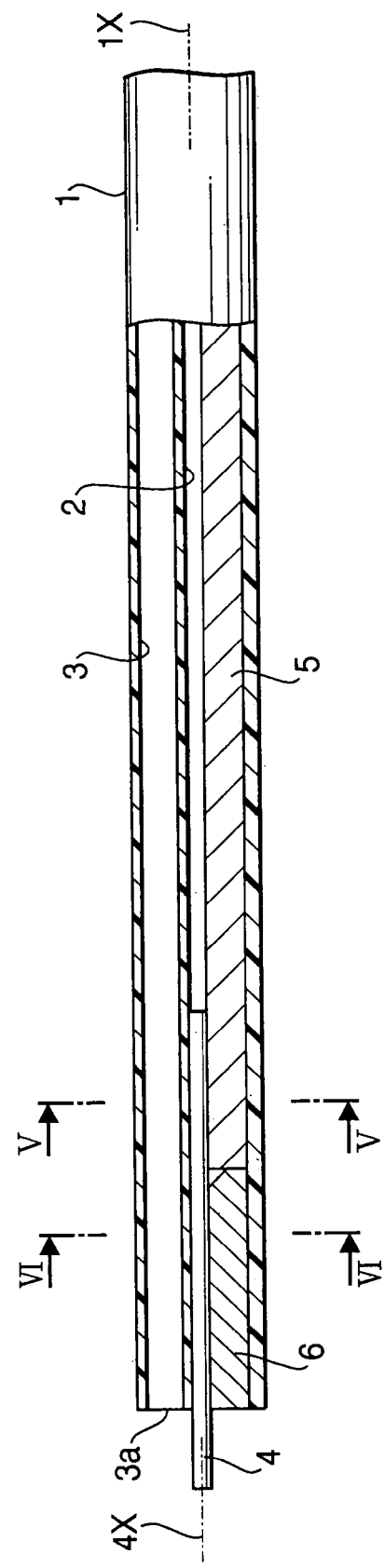
FIG. 1 is a cross-sectional side view of a neighboring portion of a distal end of a high frequency treatment tool for an endoscope in a first embodiment according to the present invention.
Figure 5:
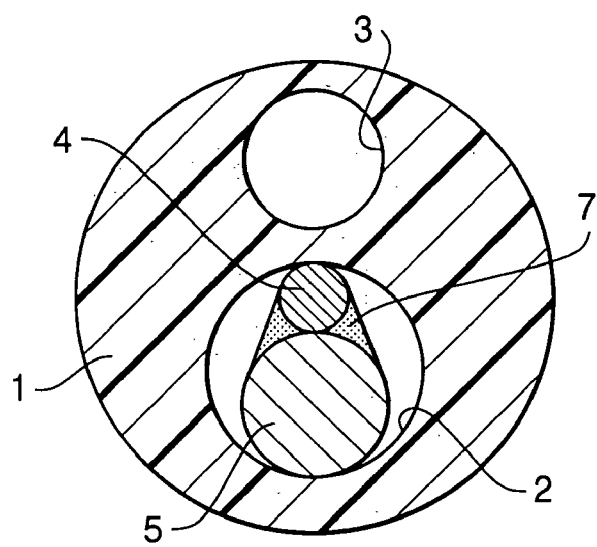
FIG. 5 is a cross-sectional view, along a V-V line shown in FIG. 1, of the high frequency treatment tool in the first embodiment according to the present invention.
Figure 6:
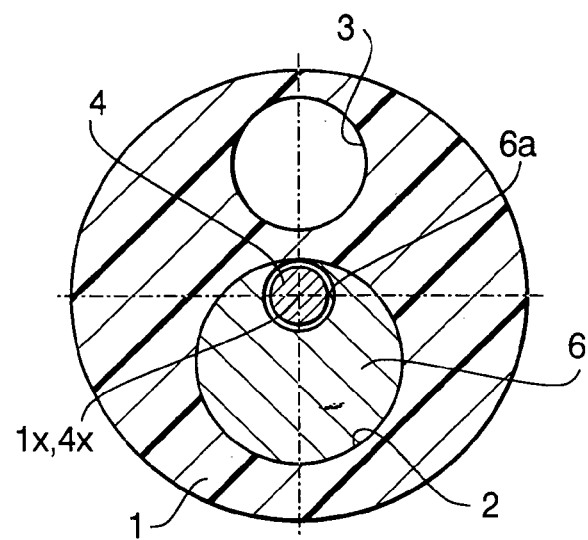
FIG. 6 is a cross-sectional view, along a VI-VI line shown in FIG. 1, of the high frequency treatment tool in the first embodiment according to the present invention.

FIG. 1 shows a neighboring portion of the distal end of the sheath 1, and FIGS. 5 and 6 are cross-sectional views thereof along a V-V line and a VI-VI line shown in FIG. 1, respectively. The high frequency electrode 4 is formed from a conductive straight metal rod such as a stainless steel rod member. The distal end of the high frequency electrode 4 is not acicular in this embodiment, yet it may be acicular, and may be pipe-shaped.

Figure 7:
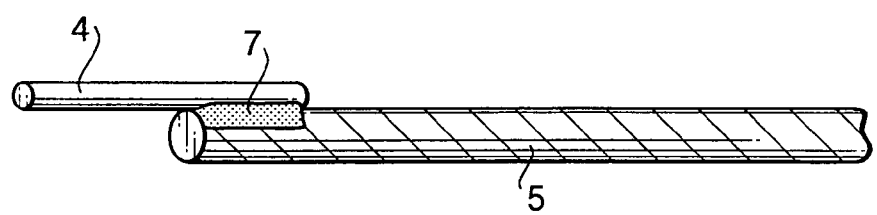
FIG. 7 is a perspective view of a joint portion between an operating wire and a high frequency electrode of the high frequency treatment tool in the first embodiment according to the present invention.

Such a high frequency electrode 4, as shown in FIG. 7, is coupled to the distal end of the operating wire 5 in parallel with each other, with each other's side faces (that is, a side face of the leading edge portion of the operating wire 5 and a side face of the rear end portion of the high frequency electrode 4) being directly fixed, for instance, by silver-alloy brazing 7 without any other connecting material. Therefore, as shown in FIG. 5, the joint portion between the operating wire 5 and the high frequency electrode 4 can be efficiently housed in the wire insertion channel 2 of the sheath 1.

If such a high frequency electrode 4 is simply projected and receded from the distal end of the sheath 1 by movement of the operating wire 5 going back and forth, the high frequency electrode 4 may be hard to use because of an unstable position of the high frequency electrode 4. For this reason, a regulating member 6 is firmly fixed to an inside of the leading edge portion of the wire insertion channel 2 in order to regulate unstable movement of the high frequency electrode 4.

Figure 8:
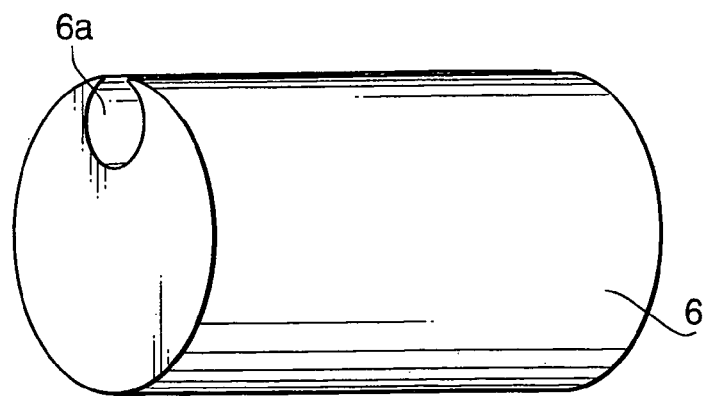
FIG. 8 is a perspective view of a simple body of a regulating member of the high frequency treatment tool in the first embodiment according to the present invention.

The regulating member 6, as shown in FIG. 8 indicating a perspective view of a simple body thereof, is formed of a cylinder with such a size as to be just fitted in the wire insertion channel 2. Near a marginal side portion of the regulating member 6, there is formed, along the axis line thereof, an electrode guide hole 6a with such a diameter that the high frequency electrode 4 can pass through the electrode guide hole 6a, yet that the operating wire 5 cannot pass through the electrode guide hole 6a. Thereby, the high frequency electrode 4, fitted into the electrode guide hole 6a, can smoothly stably move back and forth only in the axis line direction thereof.

The electrode guide hole 6a, as shown in FIG. 6, is formed such that the axis line thereof is conformed to that of the sheath 1 when the regulating member 6 is fitted into the leading edge portion of the wire insertion channel 2. As a result, the axis line 4x of the high frequency electrode 4 placed in the electrode guide hole 6a is conformed to the axis line 1x of the sheath 1.

Accordingly, when the operating wire 5 is operated at the operating portion 10 to move back and forth, as shown in FIG. 9 that is an external view of the distal end portion of the sheath 1, the high frequency electrode 4 is stably projected and receded from the distal end of the sheath 1 along the axis line of the sheath 1. As shown in FIG. 1, the maximum projecting length of the high frequency electrode 4 is restricted with the distal end of the operating wire 5 being in contact with a rear end face of the regulating member 6. The sheath 1 can squirt water from the squirt hole 3a in the distal end face thereof without being affected by projecting/receding states of the high frequency electrode 4.

Second Embodiment

FIGS. 10-14 show a high frequency treatment tool for an endoscope in a second embodiment of the present invention. In the second embodiment, as shown in FIG. 10, an axis line 1x of a sheath 1 is located completely off a wire insertion channel 2.

Figure 11:
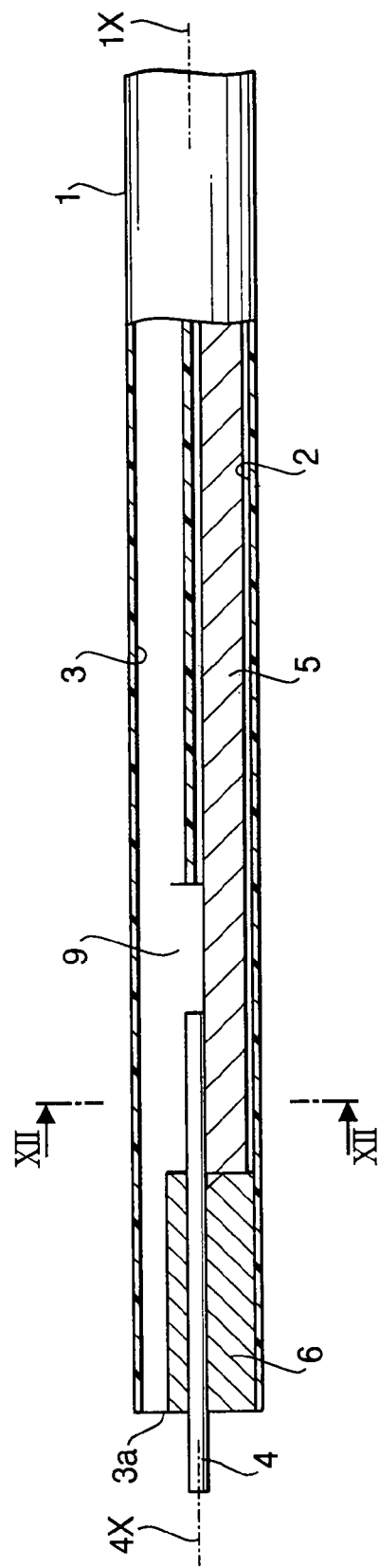
FIG. 11 is a cross-sectional side view of a neighboring portion of a distal end of the high frequency treatment tool in the second embodiment according to the present invention.
Figure 12:
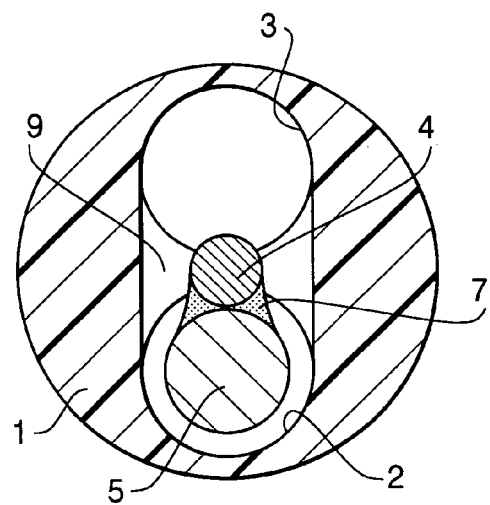
FIG. 12 is a cross-sectional view, along a XII-XII line shown in FIG. 11, of the high frequency treatment tool in the second embodiment according to the present invention.

As shown in FIG. 11 that is a cross-sectional view of the sheath 1, in the sheath 1 excluding a distal end portion thereof, there are separately provided the wire insertion channel 2 and a water channel 3. On the other hand, in the distal end portion of the sheath 1, the wire insertion channel 2 and the water channel 3 are integrated into an elongate opening 9, as shown in FIG. 12 indicating a cross-sectional view of the sheath 1 along XII-XII line in FIG. 11. A joint portion between a high frequency electrode 4 and an operating wire 5 is arranged in the elongate opening 9.

Figure 13:
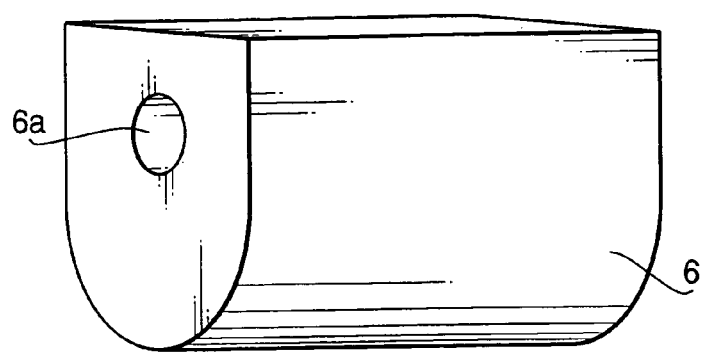
FIG. 13 is a perspective view of a simple body of a regulating member of the high frequency treatment tool in the second embodiment according to the present invention.

A regulating member 6, as shown in FIG. 13 that is a perspective view of a simple body thereof, is formed of such a shape as to fill about two thirds of the elongate opening 9. An electrode guide hole 6a penetrating through the regulating member 6 is formed such that an axis line thereof is conformed to the axis line 1x of the sheath 1 when the regulating member 6 is fitted into the elongate opening 9.

Figure 14:
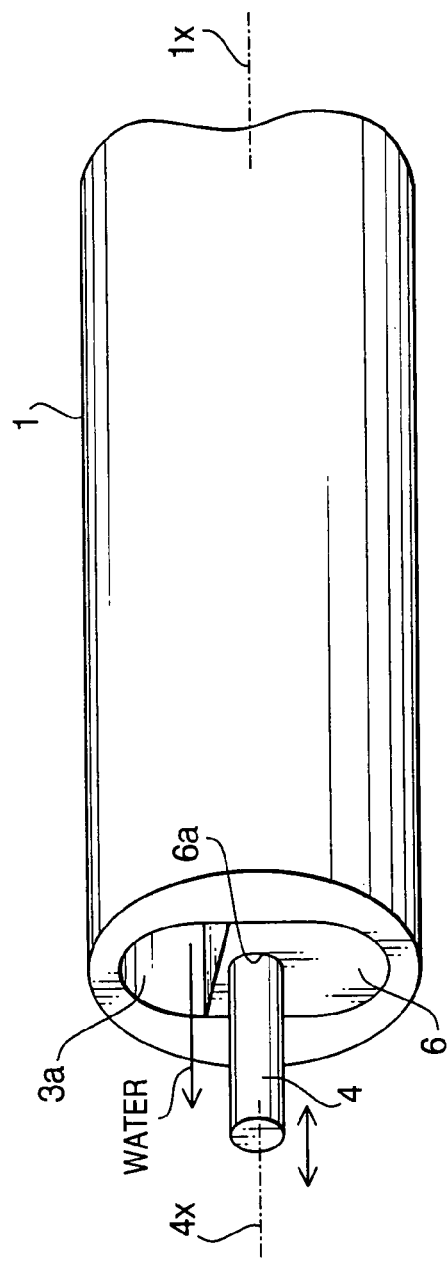
FIG. 14 is a perspective external view of the distal end portion of the high frequency treatment tool in the second embodiment according to the present invention.

Therefore, the operating wire 5 is operated at an operating portion 10 to move back and forth, as shown in FIG. 14 that is an external view of the distal end portion of the sheath 1, the high frequency electrode 4 is stably projected and receded from the distal end of the sheath 1 along the axis line of the sheath 1. As shown in FIG. 11, the maximum projecting length of the high frequency electrode 4 is restricted with the distal end of the operating wire 5 being in contact with a rear end face of the regulating member 6.

The sheath 1 can squirt water from a squirt hole 3a (a portion excluding a portion filled with the regulating member 6 in the elongate opening 9) in the distal end face thereof without being affected by projecting/receding states of the high frequency electrode 4.

Third Embodiment

Figure 15:
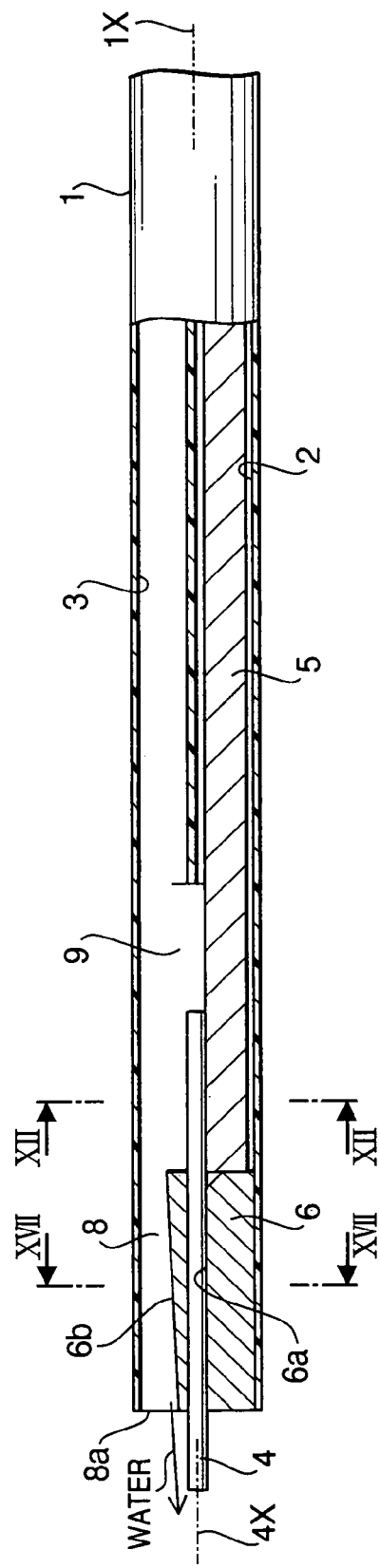
FIG. 15 is a cross-sectional side view of a neighboring portion of a distal end of a high frequency treatment tool for an endoscope in a third embodiment according to the present invention.
Figure 16:
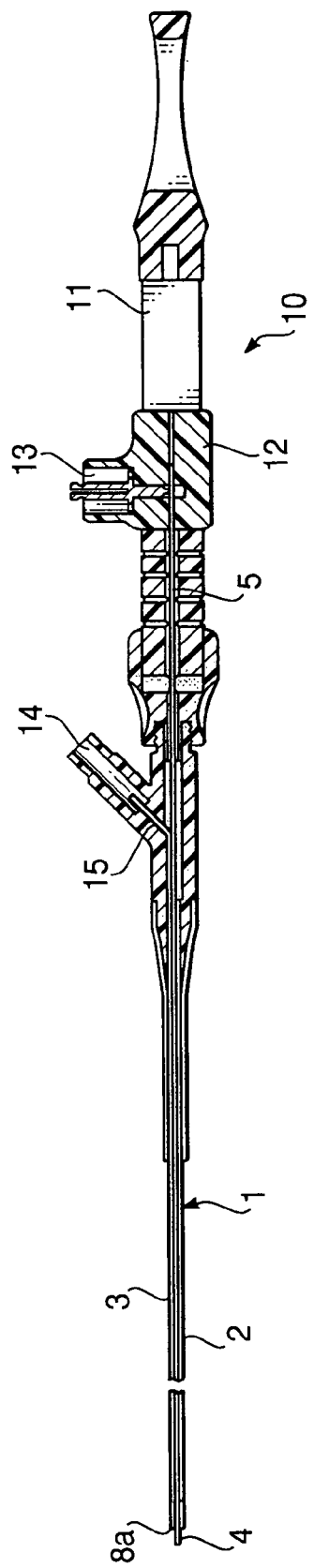
FIG. 16 is a cross-sectional side view showing the overall configuration of the high frequency treatment tool in the third embodiment according to the present invention.
Figure 17:
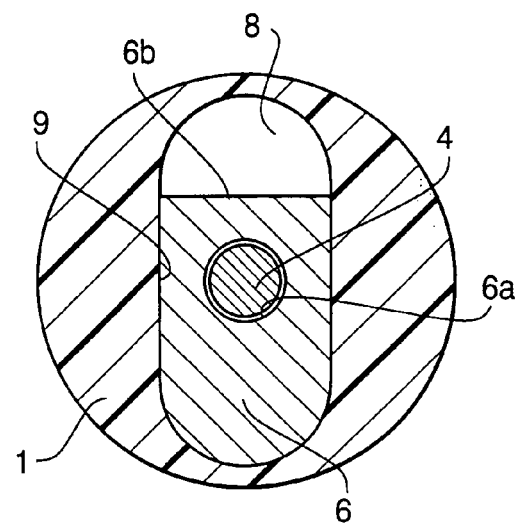
FIG. 17 is a cross-sectional view, along a XVII-XVII line shown in FIG. 15, of the high frequency treatment tool in the third embodiment according to the present invention.
Figure 18:
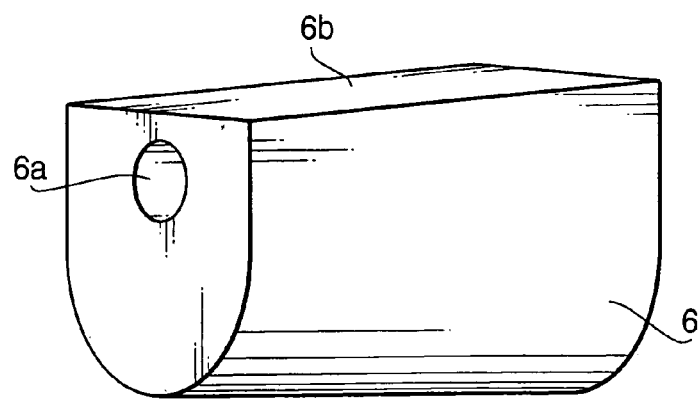
FIG. 18 is a perspective view of a simple body of a regulating member of the high frequency treatment tool in the third embodiment according to the present invention.
Figure 19:
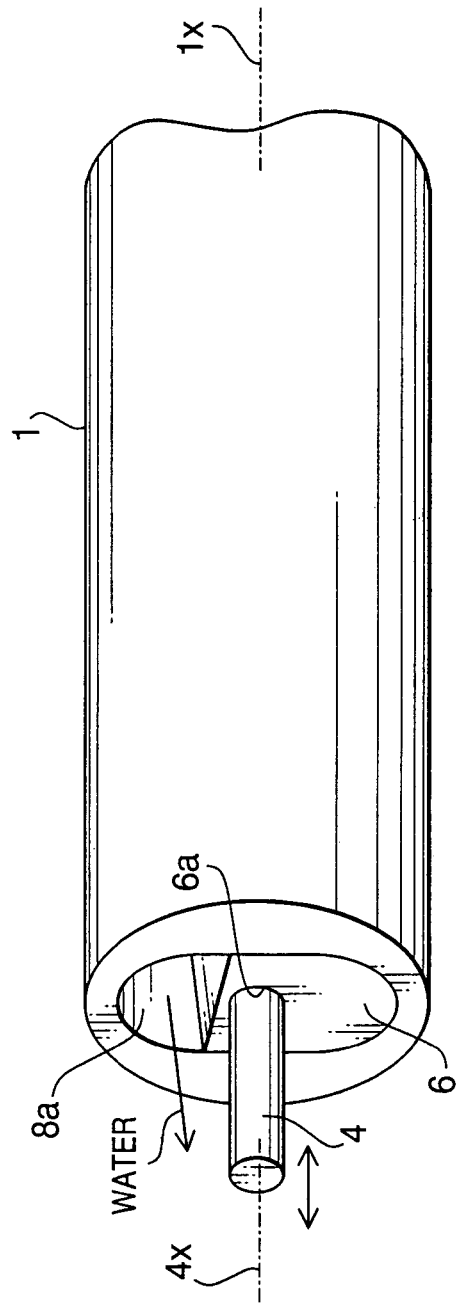
FIG. 19 is a perspective external view of the distal end portion of the high frequency treatment tool in the third embodiment according to the present invention.

FIG. 16 is a cross-sectional side view showing the overall configuration of a high frequency treatment tool for an endoscope in a third embodiment of the present invention. FIG. 15 shows a neighboring portion of a distal end of a sheath 1, and FIG. 17 is a cross-sectional view thereof along a XVII-XVII line shown in FIG. 15. It is noted that a cross-sectional view thereof along a XII-XII line shown in FIG. 15 is the same as shown in FIG. 12. FIG. 18 is a perspective view of a simple body of a regulating member 6. FIG. 19 is an external view of the distal end portion of the sheath 1.

As shown in these drawings, the high frequency treatment tool in the third embodiment has almost the same configuration as that of the high frequency treatment tool in the second embodiment. However, the high frequency treatment tool in the third embodiment is different from that in the second embodiment in the following point. As shown in FIGS. 15 and 18, in the sheath 1 in the third embodiment, there is provided a water delivering nozzle 8 that is formed as a space surrounded by an inner surface of the distal end portion of the sheath 1 and the regulating member 6. A side wall surface 6b, which forms an inner wall surface of the water delivering nozzle 8, of the regulating member 6 is shaped as such a slant that a portion, which is closer to the distal end of the sheath 1, of the side wall surface 6b of the regulating member 6 is closer to a high frequency electrode 4.

Consequently, as shown in FIGS. 15 and 19, since water squirting forward out of a squirt hole 8a is directed in such a direction as to get closer to the high frequency electrode 4 by the water delivering nozzle 8, it is possible to efficiently rinse off cauterized pieces of mucous tissues, which are generated around the high frequency electrode 4 during an incision operation, and to promptly carry out the incision operation.

The present disclosure relates to the subject matters contained in Japanese Patent Applications No. P2005-001984 and No. 2005-001985, filed on Jan. 7, 2005, which are expressly incorporated herein by reference in their entirely.

What is claimed is:

1. A high frequency treatment tool for an endoscope, comprising:
    a flexible insulating tube to be inserted into and pulled out of an accessory channel of the endoscope, the flexible insulating tube including a wire insertion channel and a water channel through which water is conveyed, the wire insertion channel and the water channel being separately formed in an axis line direction of the flexible insulating tube at a rear portion of the flexible insulating tube, to define a multi-lumen tube portion and the wire insertion channel and the water channel being integrated at a distal end portion of the flexible insulating tube to define a single-lumen tube portion having an elongate opening;
    a conductive wire configured to move back and forth in the axis line direction thereof through the wire insertion channel;
    an electrode configured to project and recede from the distal end portion of the flexible insulating tube;
    a regulator provided at the distal end portion of the flexible insulating tube, the regulator being configured to regulate movement of the electrode such that the electrode stably projects and recedes from the distal end of the flexible insulating tube;
    a nozzle formed at the distal end portion of the flexible insulating tube, the nozzle being configured to direct water conveyed through the water channel to the electrode,
    wherein the regulator is configured to regulate movement of the conductive wire such that the conductive wire is prevented from being positioned within the regulator,
    wherein at least a part of the nozzle is formed by the regulator, and
    the regulator including a penetrating hole configured to guide the electrode and prevent the conductive wire from being positioned within the regulator; and
    the regulator being formed so as to fill approximately two-thirds of the elongate opening, and
    the regulator being formed at distal end of the flexible insulating tube so as to define a water hole between an outer surface of the regulator and inner surface of the flexible insulating tube, the water hole being configured to convey water from within the flexible insulating tube,
    wherein the outer surface of the regulator is slanted towards a longitudinal axis of the electrode as the outer surface of the regulator extends towards a distal most end of the flexible insulating tube.

2. The high frequency treatment tool for an endoscope according to claim 1,
    wherein the electrode is configured to project and recede from the distal end portion of the flexible insulating tube on the axis line of the flexible insulating tube.

3. The high frequency treatment tool for an endoscope according to claim 1,
    wherein a side face of the electrode contacts and is fixed to a side face of the conductive wire.

4. The high frequency treatment tool for an endoscope according to claim 3,
    wherein a silver-alloy brazing fixes the side face of the electrode to the side face of the conductive wire.

5. The high frequency treatment tool for an endoscope according to claim 1,
    wherein the flexible insulating tube comprises an ethylene tetrafluoride resin.

6. The high frequency treatment tool for an endoscope according to claim 1,
    wherein at least one of the conductive wire and the electrode comprises a stainless steel.

7. The high frequency treatment tool for an endoscope according to claim 1, wherein the flexible insulating tube further comprises an internal longitudinal extending segment that separates the wire insertion channel and the water channel from each other to define the multi-lumen tube portion.

8. A high frequency treatment tool for an endoscope, comprising:
    a flexible insulating tube to be inserted into and pulled out of an accessory channel of the endoscope, the flexible insulating tube including a wire insertion channel and a water channel through which water is conveyed, the wire insertion channel and the water channel being separately formed in an axis line direction of the flexible insulating tube such that each of the axis lines of the wire insertion channel and the water channel is eccentric with respect to the axis line of the flexible insulating tube, and a rear portion of the flexible insulating tube comprising both the wire insertion channel and the water channel to define a multi-lumen tube portion and the wire insertion channel and the water channel being integrated at a distal end portion of the flexible insulating tube to define a single-lumen tube portion having an elongate opening;
    a conductive wire configured to move back and forth in an axis line direction thereof through the wire insertion channel;
    an electrode coupled to the conductive wire such that an axis line coinciding with a center of the electrode is eccentric with respect to an axis line coinciding with a center of the conductive wire, the electrode being configured to project and recede from the distal and portion of the flexible insulating tube on the axis line of the flexible insulating tube; and
    a regulator provided at the distal end portion of the flexible insulating tube, the regulator being configured to regulate movement of the electrode such that the electrode stably projects and recedes from the distal end of the flexible insulating tube,
    the regulator being formed so as to fill approximately two-thirds of the elongate opening,
    the regulator being formed at distal end of the flexible insulating tube so as to define a water hole between an outer surface of the regulator and inner surface of the flexible insulating tube, the water hole being configured to convey water from within the flexible insulating tube,
    a penetrating hole provided within the regulator and configured to guide the electrode, and wherein the regulator is configured to regulate movement of the conductive wire such that the conductive wire is prevented from being positioned within the regulator.

9. The high frequency treatment tool for an endoscope according to claim 8, wherein the outer surface of the regulator is slanted towards a longitudinal axis of the electrode as the outer surface of the regulator extends towards a distal most end of the flexible insulating tube.

10. The high frequency treatment tool for an endoscope according to claim 8, wherein the flexible insulating tube further comprises an internal longitudinal extending segment that separates the wire insertion channel and the water channel from each other to define the multi-lumen tube portion.

* * * * *